United States Patent [19]
Haughton et al.

[11] Patent Number: 5,562,629
[45] Date of Patent: Oct. 8, 1996

[54] CATHETER PLACEMENT SYSTEM UTILIZING A HANDLE, A SHARP, AND A RELEASABLE RETAINER MECHANISM PROVIDING RETRACTION OF THE SHARP UPON DISENGAGEMENT OF THE CATHETER FROM THE HANDLE

[76] Inventors: Victor M. Haughton, 1071 Waterville Rd., Oconomowoc, Wis. 53066; Anton H. Clemens, 5854 Schumann Dr., Madison, Wis. 53711

[21] Appl. No.: 363,127

[22] Filed: Dec. 23, 1994

Related U.S. Application Data

[63] Continuation-in-part of Ser. No. 114,473, Aug. 31, 1993, Pat. No. 5,376,075.

[51] Int. Cl.⁶ ................................................ A61M 5/178
[52] U.S. Cl. .......................... 604/158; 604/195; 604/198
[58] Field of Search ..................................... 604/192, 198, 604/110, 263, 164–171, 158, 272–274, 900

[56] References Cited

U.S. PATENT DOCUMENTS

| | | |
|---|---|---|
| 2,722,215 | 11/1955 | Dahlgren . |
| 2,841,143 | 7/1958 | Bertram . |
| 3,825,003 | 7/1974 | Kruck . |
| 4,009,716 | 3/1977 | Cohen . |
| 4,573,976 | 3/1986 | Sampson et al. . |
| 4,664,259 | 5/1987 | Landis . |
| 4,676,783 | 6/1987 | Jagger et al. . |
| 4,747,831 | 5/1988 | Kulli . |
| 4,767,413 | 8/1988 | Haber et al. . |
| 4,772,265 | 9/1988 | Walter . |
| 4,781,692 | 11/1988 | Jagger et al. . |
| 4,826,484 | 5/1989 | Haber et al. . |
| 4,838,869 | 6/1989 | Allard . |
| 4,874,382 | 10/1989 | Lindemann et al. . |
| 4,955,870 | 9/1990 | Ridderheim et al. . |
| 4,978,343 | 12/1990 | Dysarz et al. ........................ 604/195 |
| 4,994,034 | 2/1991 | Botich et al. . |
| 4,994,042 | 2/1991 | Vadher . |
| 5,000,736 | 3/1991 | Kaufhold, Jr. et al. . |
| 5,108,376 | 4/1992 | Bonaldo . |
| 5,120,319 | 6/1992 | Van Heugten et al. ............ 604/900 X |
| 5,135,505 | 8/1992 | Kaufman . |
| 5,207,647 | 5/1993 | Phelps . |
| 5,215,528 | 6/1993 | Purdy et al. . |
| 5,215,529 | 6/1993 | Fields et al. ........................ 604/900 X |
| 5,242,414 | 9/1993 | Fischell et al. ..................... 604/900 X |
| 5,273,540 | 12/1993 | Luther et al. ....................... 604/198 X |

*Primary Examiner*—John D. Yasko
*Attorney, Agent, or Firm*—Andrus, Sceales, Starke & Sawall

[57] ABSTRACT

A trocar and catheter assembly for automatically disarming the trocar after placement of the catheter into a patient's blood vessel includes a spring urging retraction of the trocar and a releasable retainer mechanism for maintaining the trocar in an extended position during insertion of the catheter into the blood vessel. The catheter is removably mounted to a handle which defines an internal passage. Disengaging the handle from the catheter after placement of the catheter into the blood vessel actuates the releasable retainer mechanism for allowing the trocar to be drawn into the handle passage under the influence of a spring, to enclose the sharpened end of the trocar after use.

22 Claims, 3 Drawing Sheets

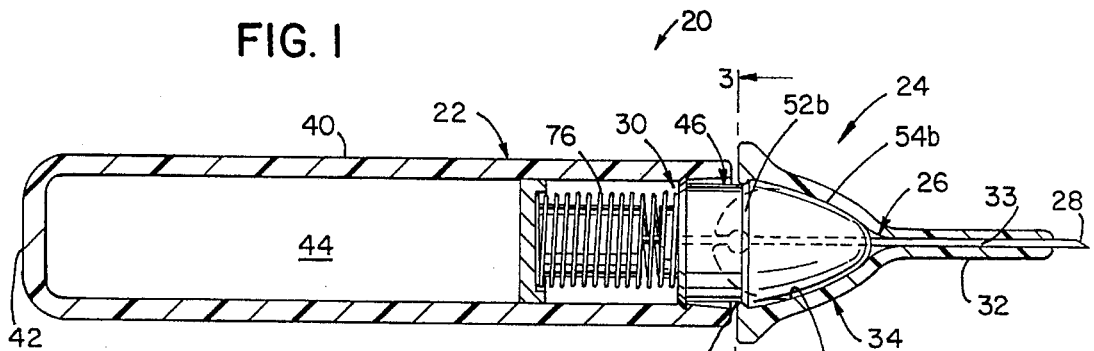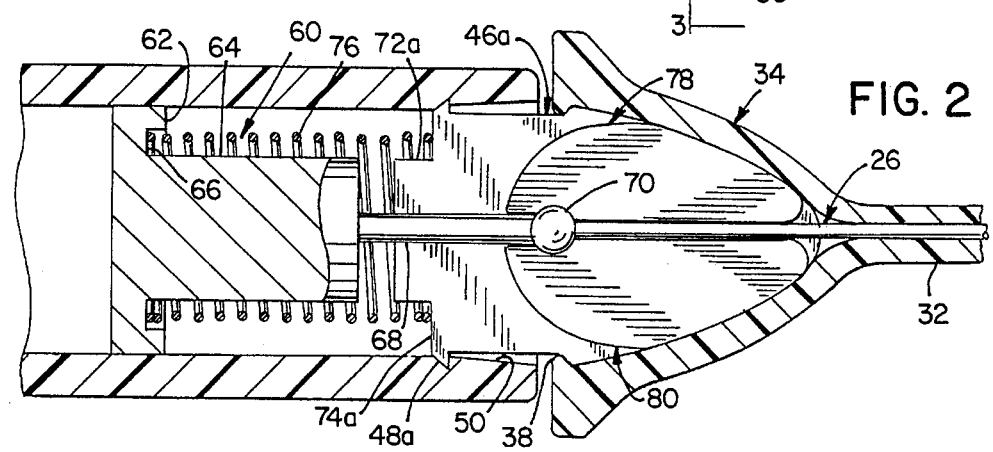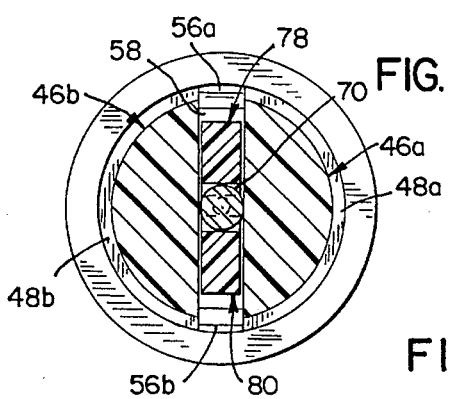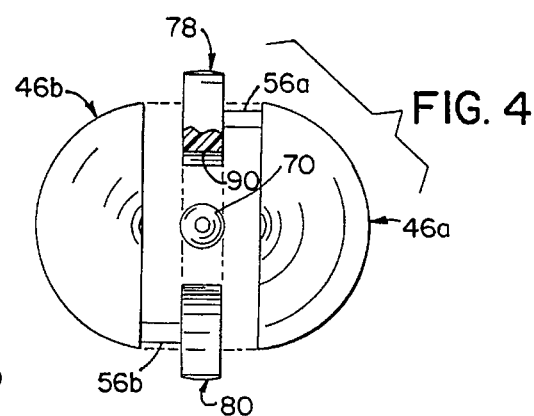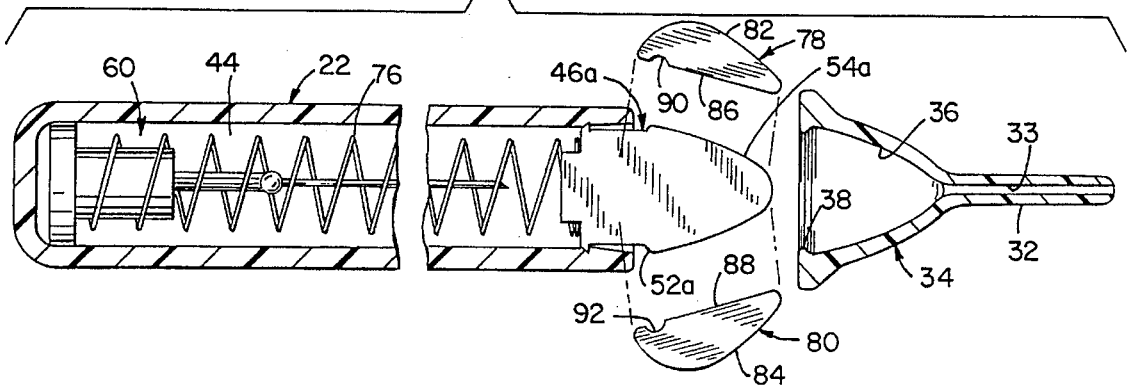

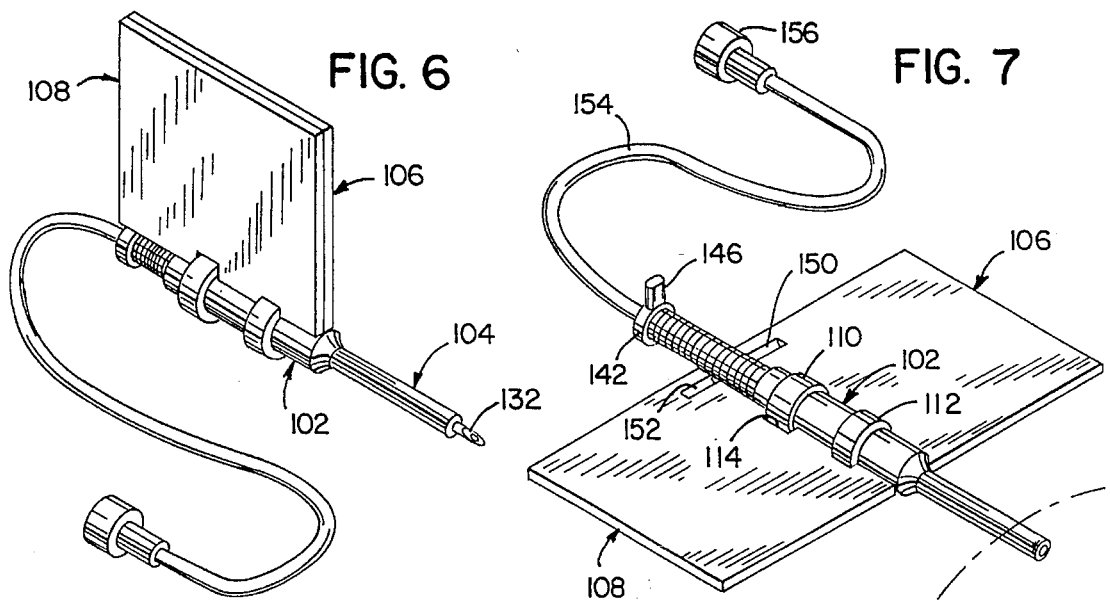
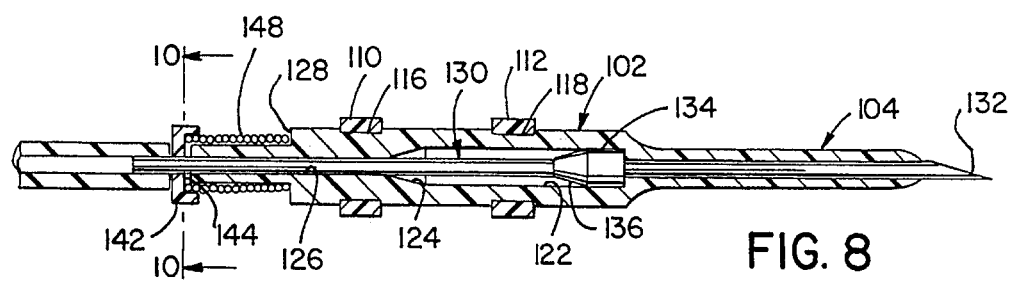
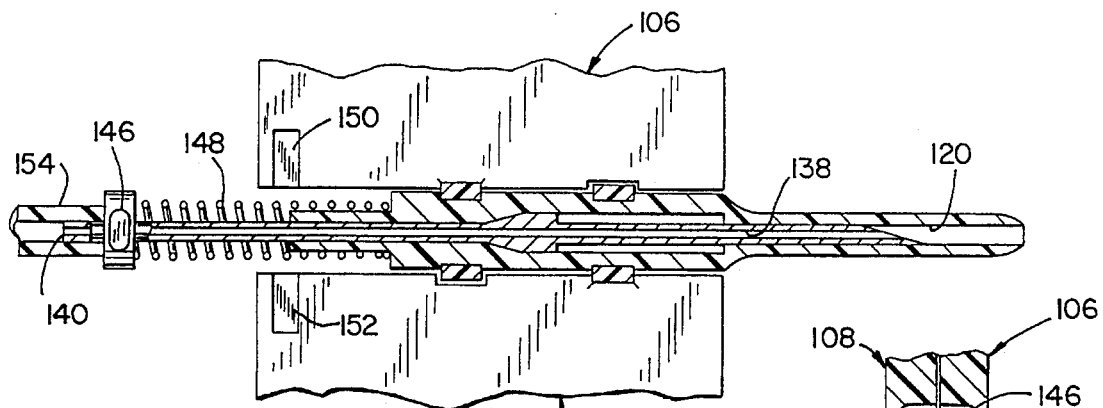
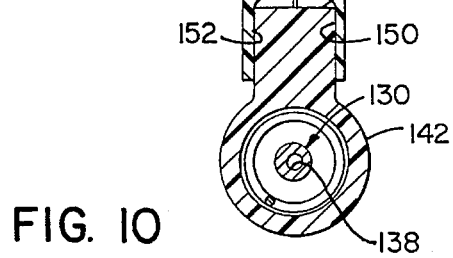

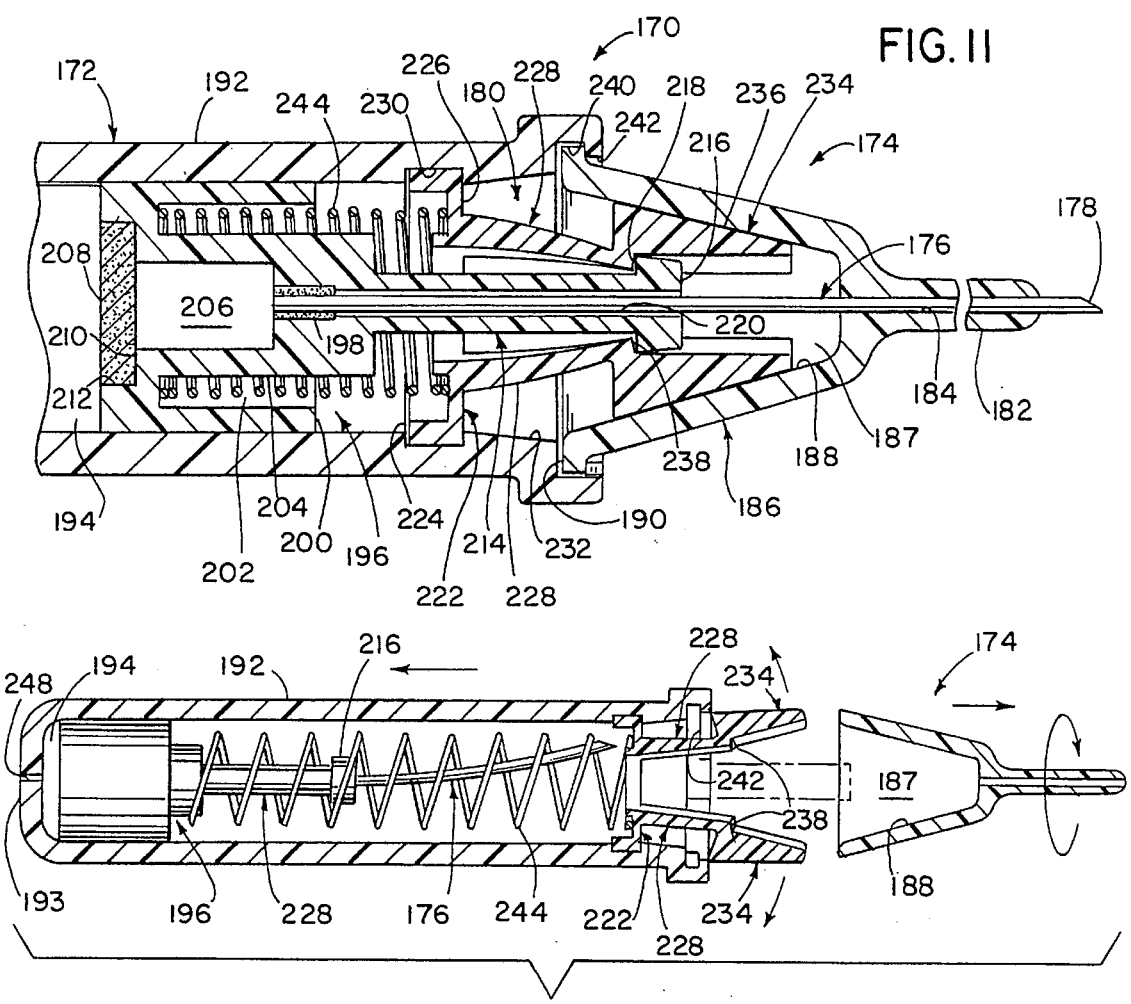
FIG. 11
FIG. 12
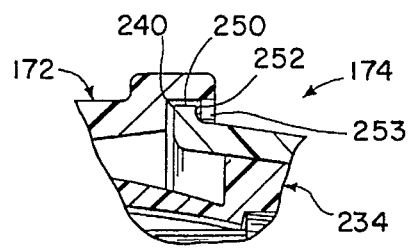
FIG. 13
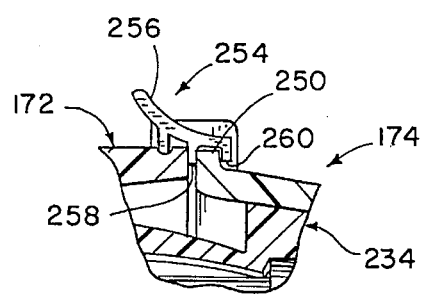
FIG. 14

CATHETER PLACEMENT SYSTEM UTILIZING A HANDLE, A SHARP, AND A RELEASABLE RETAINER MECHANISM PROVIDING RETRACTION OF THE SHARP UPON DISENGAGEMENT OF THE CATHETER FROM THE HANDLE

CROSS-REFERENCE TO RELATED APPLICATIONS

This application is a continuation-in-part of application Ser. No. 08/114,473, filed Aug. 31, 1993, now U.S. Pat. No. 5,376,075, issued Dec. 27, 1994.

BACKGROUND AND SUMMARY OF THE INVENTION

This invention relates to an intravenous catheter and trocar system, and more particularly to a system providing automatic retraction of the trocar after insertion of the catheter into a blood vessel.

Numerous patents disclose syringes which include a system for either automatically or semi-automatically retracting the syringe needle after use, to prevent accidental contact with the needle. One such syringe is shown in Lindemann, et al. U.S. Pat. No. 4,874,382, issued Oct. 17, 1989. In addition Kuuli U.S. Pat. No. 4,747,831 shows a structure for manually retracting a catheter trocar after the trocar has been used to insert the catheter into a blood vessel of a patient.

It is an object of the present invention to provide an automatic arrangement for retracting a trocar after use of the trocar to insert a catheter into a blood vessel. It is a further object of the invention to incorporate an automatic trocar retraction system into various types of catheters. Yet another object of the invention is to provide a trocar retraction system which is relatively simple in concept and inexpensive to manufacture.

In accordance with the invention, an intravenous catheter system includes a catheter defining an internal passage and a trocar having an exposed sharpened end extending from the catheter passage when in an extended position, for use in placing the catheter into a patient's blood vessel. The system further includes an insertion device for manual engagement by a user for use in inserting the sharpened end of the trocar, and thereby the catheter, into the blood vessel. The insertion device includes structure defining an internal passage, and the trocar is releasably engaged with the insertion device when the trocar is in its extended position, to extend outwardly from the internal passage and through the catheter passage. Bias means is interconnected between the insertion device and the trocar, for urging retraction of the trocar from its extended position into the catheter passage. A releasable retainer mechanism functions to retain the trocar in its extended position prior to and during insertion of the catheter and the sharpened end of the trocar into the blood vessel, and for releasing engagement between the trocar and the insertion device in response to manual manipulation of the insertion device by the user after placement of the catheter into the blood vessel. Such manual manipulation of the insertion device functions to actuate the releasable retainer mechanism, to provide retraction of the trocar from its extended position into the catheter passage under the influence of the bias means.

In one form of the invention, the insertion device comprises a handle having one or more side walls defining the internal passage, with the handle being removably engaged with the catheter to provide disengagement of the handle from the catheter in response to manual manipulation of the handle after placement of the catheter into the blood vessel. Disengagement of the handle from the insertion device actuates the releasable retainer mechanism, to release engagement between the trocar and the handle and to provide retraction of the trocar from its extended position. The bias means comprises a spring or other biasing means interconnected between the trocar and the handle, to urge withdrawal of the trocar into and through the catheter passage and into the handle passage upon disengagement of the handle from the catheter. The handle passage opens onto an end of the handle, and a plug member is mounted within the handle passage toward the open end of the handle. The plug member defines a passage through which the trocar extends when in its extended position, and the spring is interposed between the trocar and the plug member to draw the trocar through the plug member passage upon disengagement of the handle from the catheter. A retraction head is mounted to the inner end of the trocar, and the spring is located between the plug member and the retraction head. The catheter includes an enlarged outer end portion defining an open outer end leading to an internal cavity, and an inner tubular end portion defining an open inner end and an internal passage extending between the internal cavity and the open inner end. The handle is removably engaged within the internal cavity defined by the enlarged outer end portion of the catheter. The handle plug member is removably engageable within the internal cavity defined by the enlarged outer end portion of the catheter, and the releasable retainer mechanism is mounted to the plug member and interposed between the trocar and the enlarged outer end portion of the catheter. The releasable retainer mechanism functions to release engagement between the handle and the trocar upon removal of the plug member from the internal cavity defined by the enlarged outer end portion of the catheter. The trocar retraction head includes a detent disposed within the plug member passage. The releasable retainer mechanism is engaged with the trocar detent to retain the trocar in its extended position, and is disengaged from the trocar detent upon removal of the plug member from the internal cavity to provide retraction of the trocar under the influence of the spring. In one form, the releasable retainer mechanism includes a pair of retainer wings mounted within a slot formed in the plug member, and engageable between the catheter and the trocar detent when the plug member is engaged within the internal cavity defined by the enlarged outer end portion of the catheter. Removal of the plug member from the catheter internal cavity releases engagement of the retainer wings between the catheter and the trocar detent.

In another form of the invention, the insertion device includes a pair of wings pivotably mounted for movement between a first position in which the wings are positioned substantially together and a second position in which the wings are moved apart. Manual movement of the wings between their first and second positions functions to actuate the releasable retainer mechanism, to release engagement between the trocar and the insertion device and to provide retraction of the trocar from its extended position. The insertion device includes a tubular body defining the internal passage within which the trocar is mounted, and the wings are pivotably mounted to the tubular body. The catheter is mounted to and extends outwardly from the tubular body, and defines an internal passage in communication with the internal passage defined by the body. The bias means, such as a spring, functions to withdraw the sharpened end of the trocar rearwardly into the catheter passage upon release of engagement between the trocar and the insertion device in response to movement of the wings away from their first position. The internal passage defined by the tubular body opens onto the rearward end of the body, and a rearward portion of the trocar extends outwardly from the rearward end of the body. The releasable retainer mechanism includes a hub member mounted to the rearward portion of the trocar, and a detent arrangement interposed between the hub member and the wings for retaining the trocar in its extended position when the wings are in their first position, and for releasing engagement between the wings and the hub member when the wings are moved away from their first position toward their second position. The detent arrangement includes a stud mounted to the hub member, and a recess formed in each wing for receiving a portion of the stud when the wings are in their first position, and for releasing engagement between the stud and the wings when the wings are moved toward their second position. The tubular body defines an external shoulder, and the spring is interposed between the external shoulder and the hub member for urging retraction of the trocar into the catheter passage. The trocar includes a wedge-shaped stop portion disposed within the body passage, for cooperating with wedge structure disposed within the body passage for stopping rearward movement of the trocar under the influence of the bias means when engagement between the trocar and the insertion device is released. A tube may be connected to the rearward portion of the trocar, for communicating blood withdrawn from a patient to a blood collection receptacle.

The invention further contemplates a method of retracting the sharpened end of the trocar after placement of the catheter into the patient's blood vessel, substantially in accordance with the foregoing summary.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings:

FIG. 1 is a longitudinal cross-sectional view of a catheter and trocar assembly incorporating a removable handle for providing automatic retraction of the trocar into the handle after disengagement of the handle from the catheter;

FIG. 2 is an enlarged portional sectional view of the catheter and trocar assembly of FIG. 1, showing the releasable retainer mechanism maintaining the trocar in its extended position;

FIG. 3 is a section view taken along line 3—3 of FIG. 1;

FIG. 4 is an exploded end elevation view of the releasable retainer mechanism plug member and wings of the catheter and trocar system of FIG. 1;

FIG. 5 is longitudinal sectional view of the trocar and catheter assembly of FIG. 1, showing retraction of the trocar into the handle after disengagement of the handle from the catheter;

FIG. 6 is a perspective view showing a butterfly-type catheter and trocar assembly incorporating an automatic trocar retraction system according to the invention, showing the wings moved together and the trocar in its extended position;

FIG. 7 is a view of the catheter and trocar assembly of FIG. 6 showing the wings moved apart and retraction of the trocar;

FIG. 8 is a partial longitudinal sectional view of the catheter and trocar assembly of FIGS. 6 and 7, showing the trocar in its extended position;

FIG. 9 is a partial longitudinal sectional view similar to FIG. 8, showing the trocar in its retracted position;

FIG. 10 is a section view taken along line 10—10 of FIG. 8;

FIG. 11 is an enlarged partial sectional view similar to FIG. 2, showing an alternative mechanism for retaining the trocar in its extended position;

FIG. 12 is a view similar to FIG. 5, showing the embodiment of FIG. 11 and disengagement between the releasable retainer mechanism and the trocar for enabling retraction of the trocar into the handle upon disengagement of the handle from the catheter; and FIGS. 13 and 14 are partial enlarged sectional views showing alternative arrangements for releasably connecting the catheter to the handle for the embodiment of FIG. 11.

DETAILED DESCRIPTION OF THE INVENTION

Referring to FIG. 1, a retractable catheter assembly 20 generally includes a handle 22, a catheter assembly 24, a trocar 26 terminating in a sharpened outer end 28, and a releasable retainer mechanism 30.

Catheter assembly 24 includes an inner tubular portion 32 defining a passage 33, which terminates in an open inner end from which trocar outer end 28 extends when trocar 26 is in its FIG. 1 position. Catheter assembly 24 further includes an enlarged outer end portion 34 which defines an open outer end and an internal cavity 36 which communicates between passage 33 defined by inner tubular portion 32 and the open outer end defined by catheter enlarged outer end portion 34. Catheter enlarged outer end portion 34 defines a peripheral inwardly extending lip 38 disposed between the open outer end of enlarged end portion 34 and internal cavity 36 defined thereby.

Handle 22 is cylindrical in shape, defining a side wall 40, and end wall 42, and an internal passage 44 which opens onto the inner end of handle 22.

A plug 46 is mounted to handle 22 at its open inner end. Plug 46 is in the form of a pair of identical plug halves, shown in FIGS. 2-5 at 46a, 46b. Plug halves 46a, 46b are identical in construction.

Plug halves 46a, 46b each define a rear end including an outwardly extending lip 48a, 48b, respectively. Lips 48a, 48b are received within a circumferential internal groove formed in the internal surface of handle side wall 40 adjacent its open inner end, for mounting plug 46 to handle 22. The inner surface of handle side wall 40 adjacent the inner end of handle 22 is ramped, as shown at 50, for facilitating push-on insertion of plug halves 46a, 46b into the open inner end of handle 22 and engagement of lips 48a, 48b with the circumferential groove formed in the inner surface of handle side wall 40.

Referring to FIGS. 1 and 5, plug halves 46a, 46b include peripheral shoulders 52a, 52b, respectively, and nose portions 54a, 54b, respectively, extending outwardly from shoulders 52a, 52b. Nose portions 54a, 54b are shaped similarly to internal cavity 36 defined by catheter enlarged outer end portion 34.

As shown in FIGS. 3 and 4, plug halves 46a, 46b further define spacers 56a, 56b, respectively. Spacers 56a, 56b function to space plug halves 46a, 46b apart from each other when plug halves 46a, 46b are mounted to handle 22, to define a slot 58 therebetween.

With plug halves 46a, 46b mounted within the open inner end of handle 22 as described, shoulders 52a, 52b are spaced just outwardly from the inner end of handle 22 with nose portions 54a, 54b extending therefrom. Catheter 24 is engaged with plug halves 46a, 46b as shown in FIGS. 1 and 2, with catheter lip 38 being placed over shoulders 52a, 52b for retaining catheter 24 in place. Nose portions 54a, 54b of plug halves 46a, 46b, respectively are received within internal cavity 36 defined by catheter enlarged outer end portion 34.

Referring to FIG. 2, trocar 26 is mounted to a retraction head, shown generally at 60. Retraction head 60 is located within handle passage 44, and includes a flange 62 in close proximity to the inner surface defined by handle side wall 40. Flange 62 extends outwardly from a main body portion 64. A circumferential groove 66 is formed in flange 62 adjacent body portion 64.

Body portion 64 further defines a forward extension 68 through which trocar 26 extends. A circumferential spherical detent 70 is formed at the forward end of extension 68.

As shown in FIGS. 1 and 2, plug halves 46a, 46b includes bosses 72a, 72b extending rearwardly from rear surfaces 74a, 74b, respectively. A spring 76 is interposed between retraction head 60 and plug 46. The forward end of spring 76 is engaged with rear surfaces 74a, 74b of plug halves 46a, 46b, respectively, with bosses 72a, 72b received within spring 76. The rearward end of spring 76 is received within groove 66 formed in flange 62 of retraction head 60.

A pair of retainer wings, shown at 78, 80 (FIGS. 2–5) are received within slot 58 between plug halves 46a, 46b. Wings 78, 80 define outer surfaces 82, 84, respectively, and facing inner surfaces 86, 88, respectively. Retaining recesses 90, 92 are formed in facing surfaces 86, 88, respectively. When wings 78,80 are in their position as shown in FIGS. 1–3, detent 70 is received within retaining recess 90, 92. Wings 78, 80 are trapped between trocar 26 and the inner wall of catheter enlarged outer end portion 34, to thereby maintain trocar 26 in its extended position against the rearward bias exerted by spring 76.

In operation, catheter and trocar assembly 20 functions as follows. Initially, trocar 26 is in its armed condition, as shown in FIGS. 1 and 2 wherein trocar sharpened end 28 protrudes outwardly from the end of catheter inner tubular portion 32. With catheter and trocar assembly 20 in this condition, the user grasps handle 22 and enlarged outer end portion 34 of catheter 24 to place inner tubular portion 32 of catheter 24 into a patient's blood vessel. Sharpened outer end 28 of trocar 26 pierces the patient's skin for allowing inner tubular portion 32 of catheter 24 to penetrate the skin. during placement of catheter 24, trocar 26 is maintained in its extended position as shown in FIGS. 1 and 2 against the force of spring 76, by retainer wings 78, 80 remaining in their FIG. 2 position, as previously described. After inner tubular portion 32 of catheter 24 is in place in the patient's blood vessel, the user grasps handle 22 and catheter enlarged outer end portion 34 to remove handle 22 from catheter 24 with a pull-apart motion. Plug shoulders 52a, 52b are disengaged from catheter lip 38, to allow plug member nose portions 54a, 54b to be withdrawn from internal cavity 36 defined by catheter enlarged outer end portion 34. Upon such disengagement of plug 46 from catheter 24, retainer wings 78, 80 are no longer trapped between trocar 26 and the inner wall of catheter enlarged outer end portion 34, and thereby release retention of detent 70. Spring 76 then extends to its position as shown in FIG. 5, to withdraw retraction head 60 into handle passage 44, and thereby withdrawal of trocar 26 through catheter passage 33 and through internal cavity 36 defined by catheter enlarged outer end portion 34. Trocar 26 also passes rearwardly through slot 58 between plug member halves 46a, 46b, and is thereafter completely enclosed within handle passage 44 to prevent accidental contact with trocar sharpened end 28. Handle 22 with trocar 26 contained therein is then discarded, and a typical fitting is engaged with catheter enlarged outer end portion 34 for withdrawing blood from the patient or for providing intravenous introduction of a fluid into the patient's blood vessel.

FIG. 2 illustrates another embodiment of the invention, in the form of a butterfly trocar and catheter assembly 100. Assembly 100 includes a tubular body 102 which defines a forwardly extending catheter portion 104. A pair of wings 106, 108 are pivotably mounted to body 102. Referring to FIGS. 6–8, a ring 110 is mounted to wing 106, and a ring 112 is mounted to wing 108. Ring 110 passes through a slot 114 formed in wing 108, and in a like manner ring 112 passes through a slot (not shown) formed in wing 106. Rings 110, 112 are mounted within grooves 116, 118 formed in the outer surface of body 102, for pivotably mounting wings 106, 108 to body 102.

Referring to FIGS. 8 and 9, catheter portion 104 defines an internal passage 120 which opens onto the forward end of catheter portion 104. Passage 120 opens rearwardly into an internal passage 122 formed in body 102, which includes wedge structure 124 at its rearward end. A rear passage 126 is formed in body 102, extending rearwardly from wedge structure 124 and opening onto the rearward end of body 102. A circumferential external shoulder 128 is formed on body 102.

A trocar, shown generally at 130, is mounted to body 102. Trocar 130 defines a sharpened outer end 132, which extends outwardly from the end of catheter portion 104 when trocar and catheter assembly 100 is in its armed condition as shown in FIGS. 6 and 8. Trocar 130 includes a boss 134 provided with a wedge surface 136. Trocar 130 further includes a longitudinal internal passage 138 (FIG. 9) which extends between and opens onto sharpened outer end 132 and the rear end of trocar 130, shown at 140.

A hub 142 is mounted to trocar 130 adjacent its rear end 140. Hub 142 is provided with a circumferential groove 144 surrounding trocar 130. Hub 142 further includes an upstanding stud 146 (FIGS. 7, 9, and 10). A spring 148 is received within groove 144 of hub 142, and is seated at is opposite end against shoulder 128 defined by body 102. Spring 148 functions to urge trocar 130 inwardly away from its extended position.

Referring to 7, 9 and 10, a pair of slots, 150, 152 are formed in wings 106, 108, respectively. Slots 150, 152 receive stud 146 therewithin when wings 106, 108 are in their closed position, as shown in FIG. 6.

In operation, the embodiment of FIGS. 6–10 functions as follows. Prior to placement of catheter portion 104 and trocar sharpened end 132 into a patient's blood vessel, wings 106, 108 are in their closed position of FIG. 6. In this position, trocar 130 is maintained in its FIG. 8 position, with sharpened end 132 extending outwardly from the forward end of catheter portion 104, by stud 146 being received within slots 150, 152 formed in wings 106, 108, respectively as shown in FIG. 10. This maintains trocar 130 in its FIG. 8 position against the rearward biasing force applied by spring 148 to trocar 130. The user then grasps wings 106, 108 in their closed position of FIG. 2, and places catheter portion 104 into a patient's blood vessel, with trocar sharpened end 132 piercing the patient's skin to facilitate entry of catheter portion 104 into the blood vessel. Wings 106, 108 are then moved to their open position of FIG. 7 against the surface of the patient's skin. Typically, a piece of tape is then applied over wings 106, 108 to maintain catheter portion 104 in place within the blood vessel.

Upon unfolding wings 106, 108 from their FIG. 6 position and moving wings 106, 108 toward their FIG. 7 position, stud 146 is disengaged from slots 150, 152 in wings 106, 108, respectively. This releases engagement between the insertion device and trocar 130, and trocar 130 is then forced to its FIG. 9 position under the influence of spring 148 until engagement of trocar wedge surface 136 with wedge structure 124 at the rearward end of passage 122. Such movement of trocar 130 results in trocar sharpened end 132 being drawn into passage 120 defined by catheter portion 104. Fluid communication is established with the patient's blood vessel through trocar passage 138 and passage 120 defined by catheter portion 104. Withdrawal of trocar sharpened end 132 into catheter portion passage 120 prevents accidental contact with trocar sharpened end 132 after withdrawal of catheter portion 104 from the patient.

A tube 154 is connected to the rearward end of trocar 130, and a receptacle 156 is mounted to the opposite end of tube 154. In this manner, blood can be withdrawn from the patient by connecting a blood collection device to receptacle 156. Alternatively, fluid can be introduced into the patient's blood vessel by connecting an IV set to receptacle 156.

FIG. 11 illustrates an alternative embodiment to that illustrated in FIGS. 1–5. As shown in FIG. 11, a retractable catheter assembly 170 generally includes a handle 172, a catheter assembly 174, a trocar or catheter insertion member 176 terminating in a sharpened end 178, and a releasable retainer mechanism 180.

Similar to the embodiment of FIGS. 1–5, catheter assembly 174 includes a forward tubular portion 182 defining an internal passage 184, which terminates in an open forward end from which trocar outer end 178 extends when trocar 176 is in its extended FIG. 11 position. Catheter assembly 174 further includes an enlarged rear end portion 186 which defines an open rear end and an internal cavity 187 defined by an internal wall 188 which communicates between passage 184 and the open rear end defined by catheter enlarged rear end portion 186. Catheter enlarged rear end portion 186 defines a series of spaced flanges 190 which, in a manner to be explained, provide removable connection of catheter 174 to handle 172.

Handle 172 is cylindrical in shape, defining a side wall 192, an end wall 193, and an internal passage 194 which opens onto the forward end of handle 172 adjacent catheter assembly 174.

Trocar 176 is mounted at its rear end to a retraction head 196 via cement 198 or any other satisfactory mounting arrangement. Retraction head 196 includes an outer peripheral flange 200 having a cross-section corresponding to that of the inner surface of wall 192 defining passage 194, so as to slidably mount retraction head 196 within passage 194. An annular forwardly-facing recess 202 is defined between flange 200 and the outer surface of a hub 204. A cavity 206 is formed in the rear end of hub 204, and a hydrophobic air vent filter 208 is mounted to the rear end of retraction head 196 by a press fit within a mounting space defined by a shoulder 210 and an internal wall 212.

A tubular detent structure 214 extends forwardly from the forward end of retraction head hub 204. Detent structure 214 terminates in a forward detent head 216 defining a rearwardly facing shoulder 218. Detent structure 214 further defines a longitudinal passage 220 through which trocar 176 extends.

Releasable retainer mechanism 180 includes a base 222 having an outer ring 224 and an annular intermediate section 226. A series of flexible, resilient retaining fingers 228 are mounted to and extend forwardly from the inner end portion of base intermediate section 226.

Base 222 is mounted to handle 172 via outer ring 224 being disposed within an annular slot 230 formed in the inner surface of handle side wall 192. Handle side wall 192 includes a tapered internal end wall section 232 extending between the open forward end of handle 172 and slot 230. Outer ring 224 of base 222 is engaged within slot 230 by engaging ring 224 with tapered end wall section 232 and exerting a push-on force on base 222. A series of slots (not shown) may be formed in ring 224 and/or intermediate section 226, so as to enable ring 224 to flex inwardly during such movement through the passage defined by tapered end wall section 232. When base 222 has passed completely through tapered end wall section 232, ring 224 returns to its original condition and is seated within slot 230, for securing releasable retainer mechanism 180 adjacent the open forward end of handle 172 such that fingers 228 extend outwardly therefrom.

At least two fingers 228 extend forwardly from base 222, although any satisfactory number of fingers 228 could be used. Each finger 228 includes a release chuck section 234 at its outer end. Each release chuck section 234 includes an outer surface 236 having a taper corresponding to the taper of catheter wall 188, and a forwardly facing shoulder 238. Fingers 228 are movable between a retaining position as shown in FIG. 11 and a release position as shown in FIG. 12. The resiliency of fingers 228 biases finger 228 toward their FIG. 12 release position, maintaining engagement of release chuck section outer surfaces 236 with catheter wall 188. When in their retaining position of FIG. 11, fingers 228 are forced by catheter wall 188 to a convergent position in which each shoulder 238 engages shoulder 218 formed on detent structure head portion 216, for maintaining trocar 176 in its extended position.

Handle 172 is provided at its forward end with an annular groove 240 which receives flanges 190 at the rearward end of catheter 174. A series of spaced inwardly extended flanges 242 are formed at the forwardmost end of handle 172, and the spaces between flanges 242 receive flanges 190 formed on the rearward end of catheter 174. With this arrangement, a "bayonet" type connection is provided between catheter 174 and handle 172, with flanges 190 and 242 engaging each other with a push-on and twist motion. Likewise, catheter 174 is removable from handle 172 by a twisting motion in which catheter flanges 190 are aligned with the spaces between flanges 242.

A spring 244 extends between base 222 and retraction head 196, for urging retraction head 196 rearwardly relative to base 222.

In operation, and with reference to FIGS. 11 and 12, catheter assembly 170 functions as follows. Initially, catheter assembly 170 is in its assembled condition of FIG. 11. In this condition, shoulders 238 of finger release chuck sections 234 engage shoulder 218 on detent head 216, to maintain trocar 176 in its extended position in which its sharpened end 178 extends outwardly from the end of catheter 174. Trocar 176 is maintained in its extended position against the bias of spring 244 which urges retraction head 196, and thereby trocar 176, rearwardly toward a retracted or withdrawn position. The user then grasps handle 172 and, utilizing trocar sharpened end 178, places catheter forward end 182 into the patient's blood vessel. Blood then flows rearwardly through trocar 176 into cavity 206 formed in retraction head hub 204. Air located within cavity 206 escapes through filter 208 into passage 194, and the hydrophobic nature of filter 208 prevents blood from flowing therethrough into passage 194. Retraction head 196 and handle side wall 192 are formed of a translucent or transparent material, such that the presence of blood within cavity 206 can be visibly detected by the user from the exterior of handle 172. When a milky or cloudy plastic material is employed, the presence of blood in cavity 206 appears as a darkened area at cavity 206, which is viewed through the material of handle side wall 192 and retraction head 196 to indicate that the blood vessel has been punctured.

As soon as the user has detected that the patient's blood vessel has been punctured as set forth above, the user disengages catheter 174 from handle 172 by the twisting motion described previously, in which catheter flanges 190 are aligned with the spaces between handle flanges 242. If necessary, the user then exerts a pull-off motion to separate catheter 174 from handle 172. Alternatively, the outward and forward biasing force exerted by finger release chuck portions 234 against internal wall 188 of catheter 174 functions to separate catheter 174 from handle 172.

Even before catheter 174 is fully released from engagement with finger release chuck sections 234, engagement between finger shoulders 238 and detent head shoulder 218 is released, at which time spring 244 functions to propel retraction head 196 rearwardly within handle passage 194 toward end wall 193, to draw trocar 176 into passage 194 such that trocar sharpened end 178 is located rearwardly of base 222. Fingers 228 then move to their release position of FIG. 12, and retraction head 196 and trocar 176 are located within handle passage 194. Spring 244 functions to retain retraction head 196 in its retracted FIG. 12 position, to prevent trocar 176 from subsequently falling out of handle passage 194.

During rearward movement of retraction head 196, an air vent 248 formed in handle end wall 193 enables air to escape from handle passage 194 rearwardly of retraction head 196.

As an added precaution, trocar 176 is pre-bent to a configuration as shown in FIG. 12, with such bending being located forwardly of the forward end of detent head 216. When catheter assembly 170 is in its assembled FIG. 11 position, engagement between trocar 176 and catheter forward end 182 overcomes such pre-bending of trocar 176 to straighten trocar 176 or, if the material of catheter 174 cannot so function, catheter 174 yields to the prebending of the forward portion of trocar 176. In either event, upon disengagement of catheter 174 from handle 172 and retraction of trocar 176 into handle passage 194, the pre-bending of trocar 176 orients the forward end of trocar 176 such that its sharpened end 178 is out of alignment with the passage in base 222 through which trocar 176 is withdrawn, and such that sharpened end 178 is in alignment with base intermediate section 226. This functions to ensure that, even if spring 244 were removed or disabled, trocar 176 could not be withdrawn from handle passage 194 without destruction of releasable retainer mechanism 180.

FIG. 13 illustrates an alternative arrangement for releasably securing catheter 174 to handle 172. In this arrangement, catheter 174 and handle 172 have a conventional luer lock arrangement in the form of a pair of spaced tabs 250 provided at the rearward end of catheter 174 and a pair of female threads 252 provided at the forward end of handle 172 defined by a thread wall 253. Catheter tabs 250 and threads 252 are engaged via a ½ to ¾ turn screw-on or twist-on motion, which functions to releasably secure catheter 174 to handle 172. When the user desires, catheter 174 is disengaged from handle 172 by a reverse ½ to ¾ turn screw-off or twist-off motion on catheter 174. This motion results in slight forward movement of catheter 174, to assist in disengaging release chuck sections 234 from catheter wall 188. The above-described sequence of events then function to withdraw trocar 176.

FIG. 14 illustrates yet another alternative arrangement for releasably securing catheter 174 to handle 172. In this arrangement, catheter 174 is again provided with a continuous annular flange 250 at its rearward end. One or more, and preferably two, manually actuable latch members 254 are pivotably mounted at the forward end of handle 172, and each includes a finger-actuated end 256 and a pair of spaced tabs 258, 260 which receive catheter flange 250. When the user wishes to disengage catheter 174 from handle 172, the user engages finger-actuated end 256 and depresses same toward handle side wall 192, at which time latch 254 pivots so as to enable the forward bias on cannula 174 from finger release chuck sections 234 to propel cannula 174 forwardly. Preferably, the two latch members 254 are mounted to opposite sides of the forward end of handle 172.

Various alternatives and embodiments are contemplated as being within the scope of the following claims particularly pointing out and distinctly claiming the subject matter regarded as the invention.

We claim:

1. In an intravenous catheter system including a catheter defining an internal passage and a catheter insertion member having an exposed sharpened end extending from the catheter passage when in an extended position, for use in placing the catheter into a blood vessel of a patient, the improvement comprising:

an insertion device releasably connected to the catheter for manual engagement by a user for use in inserting the sharpened end of the catheter insertion member into the patient's blood vessel to establish communication therewith by the catheter, the insertion device including structure defining an internal passage, wherein the catheter insertion member is releasably engaged with the insertion device when in its extended position so as to extend outwardly from the internal passage and through the catheter passage;

bias means interconnected between the insertion device and the catheter insertion member for urging retraction of the catheter insertion member from its extended position toward the insertion device internal passage; and a releasable retainer mechanism interposed between the catheter and the catheter insertion member for retaining the catheter insertion member in its extended position prior to and during insertion of the catheter and the catheter insertion member sharpened end into the blood vessel, and for releasing engagement between the catheter insertion member and the insertion device in response to disengagement of the catheter from the insertion device after placement of the catheter into the blood vessel, to provide retraction of the catheter insertion member from its extended position into the insertion device passage under the influence of the bias means.

2. The improvement of claim 1, wherein the bias means comprises a spring interconnected between the catheter insertion member and the insertion device so as to urge withdrawal of the catheter insertion member into and through the catheter passage and into the passage of the insertion device upon disengagement of the insertion device from the catheter.

3. The improvement of claim 1, wherein the insertion device comprises a handle having an internal wall defining the passage, wherein the handle defines first and second ends and wherein the handle passage opens onto the first end of the handle, and wherein the handle further includes a plug member mounted within the handle passage at the first end of the handle, the plug member defining a passage through which the catheter insertion member extends when in its extended position, and wherein the bias means is interposed between the catheter insertion member and the plug member to draw the catheter insertion member through the plug member passage and into the handle passage upon disengagement of the handle from the catheter.

4. The improvement of claim 3, wherein the catheter insertion member is mounted to a retraction head disposed within the handle passage, and wherein the bias means is interposed between the plug member and the retraction head for urging the catheter insertion member into the handle passage.

5. The improvement of claim 1, wherein the catheter includes an enlarged rear end portion defining an open outer end leading to an internal cavity, and a forward tubular end portion defining an open forward end and an internal passage extending between the internal cavity and the open forward end, and wherein the insertion device is removably engaged within the internal cavity defined by the enlarged rear end portion of the catheter.

6. The improvement of claim 5, wherein the insertion device comprises a handle having an internal wall defining the passage, the handle defining first and second ends, and wherein the handle passage opens onto the first end of the handle, wherein the handle further includes a plug member mounted at the first end of the handle and extending therefrom, wherein the plug member is removably engageable within the internal cavity defined by the enlarged rear end portion of the catheter, and wherein the releasable retainer mechanism is mounted to the plug member and interposed between the catheter insertion member and the enlarged rear end portion of the catheter, and functions to release engagement between the handle and the catheter insertion member upon removal of the plug member from the internal cavity defined by the enlarged rear end portion of the catheter.

7. The improvement of claim 6, wherein the catheter insertion member extends through a passage formed in the plug member and includes a detent disposed within the plug member passage, and wherein the releasable retainer mechanism is engaged with the catheter insertion member detent when the plug member is engaged within the internal cavity defined by the enlarged rear end portion of the catheter to retain the catheter insertion member in its extended position, and wherein the releasable retainer mechanism is disengaged from the catheter insertion member detent upon removal of the plug member from the internal cavity to provide retraction of the catheter insertion member from its extended position under the influence of the bias means.

8. The improvement of claim 7, wherein the plug member passage comprises a slot, and wherein the releasable retainer mechanism comprises a pair of retainer wings mounted within the slot and engageable between the catheter and the catheter insertion member detent when the plug member is engaged within the internal cavity defined by the enlarged rear end portion of the catheter, and wherein removal of the plug member from the internal cavity functions to release engagement of the retainer wings between the catheter and the catheter insertion member detent.

9. The improvement of claim 1, wherein the releasable retainer mechanism includes a detent associated with the catheter insertion member and a release mechanism mounted to the handle and movable between a retaining position in which the detent is engaged and a release position in which the detent is disengaged, and wherein disengagement of the catheter from the handle causes the release mechanism to move from its retaining position to its release position to disengage the detent and to enable retraction of the catheter insertion member under the influence of the bias means.

10. The improvement of claim 9, wherein the catheter is releasably connected to the insertion device by interlocking structure provided on the insertion device and on the catheter.

11. The improvement of claim 10, wherein the insertion device comprises a handle defining first and second ends and includes an internal wall defining the passage, and wherein the handle passage opens onto the first end of the handle.

12. The improvement of claim 11, wherein the interlocking structure comprises bayonet-type connection structure interposed between the catheter and the handle first end for disengaging the catheter from the handle by a rotating motion.

13. The improvement of claim 11, wherein the interlocking structure comprises a flange formed on the catheter, a recess formed at the handle first end for receiving the flange, and one or more protrusions extending inwardly into the recess for engaging the flange to retain the catheter in engagement with the handle, and wherein the flange is movable over the protrusions with a pull-off motion to disengage the catheter from the handle.

14. The improvement of claim 11, wherein the interlocking structure comprises a flange formed on the catheter and a manually actuable latch mechanism movable to a latching position for engaging the flange to retain the catheter in engagement with the handle, and a release position for disengaging the flange to disengage the catheter from the handle.

15. The improvement of claim 9, wherein the catheter includes an enlarged rear end portion defining an open rear end leading to an internal cavity, and a forward tubular end portion defining an open forward end and an internal passage extending between the internal cavity and the open forward end, and wherein the handle is removably engaged within the internal cavity defined by the enlarged rear end portion of the catheter, wherein the release mechanism includes two or more fingers resiliently movably mounted to the handle and engaged with the wall defining the internal cavity of the enlarged rear end portion of the catheter when the release mechanism is in its retaining position for engaging the detent associated with the catheter insertion member, wherein the fingers are biased toward a release position and are retained in a retaining position by engagement with the catheter wall, and wherein disengagement of the catheter from the handle results in the fingers moving to their release position to disengage the detent and enable withdrawal of the catheter insertion member under the influence of the bias means.

16. The improvement of claim 15, wherein the insertion device comprises a handle having an internal wall defining the passage, and wherein the handle defines first and second ends, wherein the handle passage opens onto the first end of the handle, and wherein the release mechanism is mounted to the handle such that the fingers extend from the handle first end.

17. The improvement of claim 16, wherein the fingers extend from a release mechanism base disposed within the handle passage and mounted to the handle.

18. The improvement of claim 9, wherein the insertion device comprises a handle having an internal wall defining the passage, wherein the handle defines first and second ends, and wherein the handle passage opens onto the first end of the handle, wherein the release mechanism includes a base mounted to the handle via an internal slot formed in the handle adjacent the handle first end.

19. The improvement of claim 18, wherein the handle includes a tapered internal wall extending inwardly to the internal slot from the handle first end, and wherein the release mechanism base is engageable with the internal slot via push-on engagement with the tapered wall.

20. The improvement of claim 9, wherein the catheter insertion member is mounted to a retraction head, wherein the bias means acts on the retraction head for urging retraction of the catheter insertion member, wherein the retraction head includes a cavity for receiving blood from the patient after the catheter insertion member is placed into the patient's blood vessel, and wherein the insertion device and the retraction head are constructed such that the presence of blood within the cavity provides a visual indication to the operator that the catheter insertion member has been placed into the patient's vein.

21. The improvement of claim 1, wherein the catheter insertion member comprises an elongated needle and wherein the releasable retainer mechanism includes a passage through which the needle is withdrawn under the influence of the bias means during movement into the insertion device passage, and wherein the needle is constructed and arranged such that, when the needle is withdrawn into the insertion device passage, the sharpened end of the needle is moved out of alignment with the releasable retainer mechanism passage.

22. In an intravenous catheter system including a catheter defining an internal passage and a catheter insertion member having an exposed sharpened end and extending from the catheter passage when in an extended position, for use in placing the catheter into a blood vessel of a patient, a method of retracting the sharpened end of the catheter insertion member after placement of the catheter into the blood vessel, comprising the steps of:

provifing an insertion device including structure defining an internal passage, wherein the catheter insertion member is associated with the insertion device;

releasably engaging the catheter with the insertion device when the catheter insertion member is in its extended position so that the catheter insertion member extends outwardly from the internal passage and through the catheter passage;

urging retraction of the catheter insertion member from its extended position into the catheter passage while maintaining the catheter insertion member in its extended position;

inserting the sharpened end of the catheter insertion member into the blood vessel to establish communication therewith via the catheter, by manual operation of the insertion device; and manually disengaging the catheter from the insertion device after placement of the catheter into the blood vessel, in order to release maintenance of the catheter insertion device in its extended position and to retract the catheter insertion member from its extended position into the catheter passage.

* * * * *